Feb. 28, 1950 V. REITER, JR Plant Pat. 925

FUCHSIA PLANT

Filed Nov. 19, 1948

INVENTOR
Victor Reiter, Jr.
BY: Harper Allen
ATTORNEY

Patented Feb. 28, 1950

Plant Pat. 925

UNITED STATES PATENT OFFICE

925

FUCHSIA PLANT

Victor Reiter, Jr., San Francisco, Calif.

Application November 19, 1948, Serial No. 61,070

1 Claim. (Cl. 47—60)

Figures 1, 2:
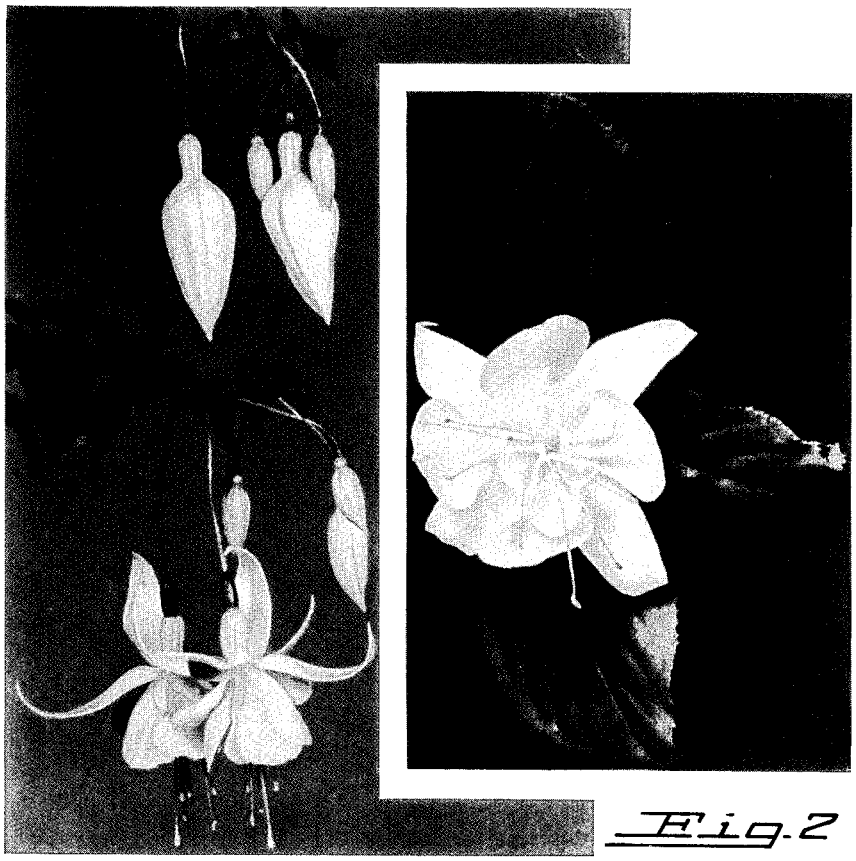

This invention relates to a new and improved fuchsia, and more particularly to a white fuchsia having fine growth characteristics and a desirable whiteness of color. One of the principal objects of the inventor in producing this fuchsia was to obtain a plant having the desirable growth characteristics and warm air tolerance of the fuchsia Whitemost (Niederholzer) and the non-bi-color whiteness of the fuchsia Ave Maria (Reiter, Sr.).

The fuchsia was derived as a hybrid from the above identified strains of near white fuchsias, and from a group of plants one seedling of exceptional quality was selected after competitive tests in full sun in San Francisco, California. The seedling retained demonstrated the great vigor and fine flowers of this new fuchsia hybrid.

The plant has foliage of a deeper green and wood of a firmer quality than previous varieties in this white fuchsia group, and resembles in habit the desirable type of growth characteristics of double purple varieties of fuchsias. The plant is of a small medium size growth with arching stiff branches and freely produced laterals. The blossom is double flowered and is slightly flushed with the palest shade of rose madder (Horticultural Color Chart 23/3), which is slightly intensified at the base of the petals. In very deep shade the flowers are pure white but under heavy feeding and cultivated in good light they have a faint flush.

In the accompanying drawings, Figure 1 illustrates typical branch tips with the closed buds at the upper portion of the figure and with both buds and opened flowers in the lower branch tip shown. Figure 2 illustrates a view of a fully opened flower with leaves in the background. In Figure 1 the fuchsia is shown at about three-fourths of its actual size, while Figure 2 is only slightly reduced from a full-size flower.

A detail description of this new variety of fuchsia follows:

Habit of growth: Strong medium-sized growth with naturally arching stiff branches. Laterals are freely produced.

Foliage: Medium size, darker green, more sharply dentate and less rugose than previous varieties in the near white group.

Bud: Medium to long, ovoid, greenish white.

Flower: Double, medium size for the genus, and large for the pale self-colored group to which it belongs.

Flower stem: Medium to long, light green to brown in sunlight.

Ovary: Medium size, ovoid, light green.

Hypanthium (tube): Medium length, greenish white with rosy flush.

Petals (corolla): Double with the doubleness variable. Early flowers and fertilized plants are quite double, and normal doubleness is over fifteen petals. Late flowers are occasionally single, often semi-double. Petals are of varying size. The full corolla is approximately half the length of the sepals. Petals are incurved globular in the best flowers, more spreading in others. The petals are faintly flushed rose madder (Horticultural Color Chart 23/3) with slightly deeper coloring in the veining at the base.

Style: Long and white.

Stamens: Pale fuchsia purple.

Parentage: The parentage of this fuchsia is Ave Maria (Reiter, Sr.) ♀, and Whitemost (Niederholzer) ♂.

It will be realized that the foliage and flowers will vary considerably with the seasons and growing conditions, however, the fuchsia is clearly differentiated from previous varieties of so-called white fuchsias by its exceptional growth characteristics, its warm air tolerance and the non-bi-color whiteness of its flowers.

I therefore point out and distinctly claim as my invention and discovery:

The new variety of white fuchsia plant herein described and illustrated, characterized by its vigorous and floriferous growth, its heat tolerance, its deep green foliage, its firm wood, and the whiteness of its flowers.

VICTOR REITER, JR.

No references cited.